United States Patent [19]
Alleyne

[11] Patent Number: 5,437,672
[45] Date of Patent: Aug. 1, 1995

[54] SPINAL CORD PROTECTION DEVICE

[76] Inventor: Neville Alleyne, 9687 Claiborne Sq., La Jolla, Calif. 92037

[21] Appl. No.: 296,857

[22] Filed: Aug. 26, 1994

Related U.S. Application Data

[63] Continuation of Ser. No. 975,106, Nov. 12, 1992, abandoned.

[51] Int. Cl.[6] ............................................. A61B 17/56
[52] U.S. Cl. ....................................... 606/61; 606/69; 606/70
[58] Field of Search .................................. 606/60–71, 606/86–98, 100, 102; 623/16, 17

[56]         References Cited
         U.S. PATENT DOCUMENTS

| | | | |
|---|---|---|---|
| 3,256,877 | 6/1966 | Haboush | 606/67 |
| 3,693,616 | 9/1972 | Roaf | 606/61 |
| 4,013,078 | 3/1977 | Feild | 606/1 |
| 4,705,031 | 11/1987 | Wolter | 606/69 |
| 4,773,402 | 9/1988 | Asher | 606/61 |
| 4,794,918 | 1/1989 | Wolter | 606/69 |
| 4,973,332 | 11/1990 | Kummer | 606/67 |
| 5,000,166 | 3/1991 | Karpf | 606/61 |
| 5,041,113 | 8/1991 | Biedermann | 606/71 |
| 5,108,395 | 4/1992 | Laurain | 606/71 |
| 5,108,399 | 4/1992 | Eitenmuller | 606/77 |
| 5,113,685 | 5/1992 | Asher | 606/101 |
| 5,139,498 | 8/1992 | Astudillo | 606/69 |
| 5,242,443 | 9/1993 | Kambin | 606/61 |
| 5,261,908 | 11/1993 | Campbell | 606/61 |
| 5,366,455 | 11/1994 | Dove | 606/61 |

FOREIGN PATENT DOCUMENTS 1004625  4/1952  France ................ 606/61

Primary Examiner—Michael A. Brown
Attorney, Agent, or Firm—Knobbe, Martens, Olson & Bear

[57]        ABSTRACT

A biocompatible protection device is disclosed to prevent the postoperative formation of adhesions to the spinal dura of a vertebrate comprising a shield adapted to fit onto at least one lamina of at least one vertebrae and wherein said shield is positioned on the posterior surface of the vertebral column.

7 Claims, 4 Drawing Sheets

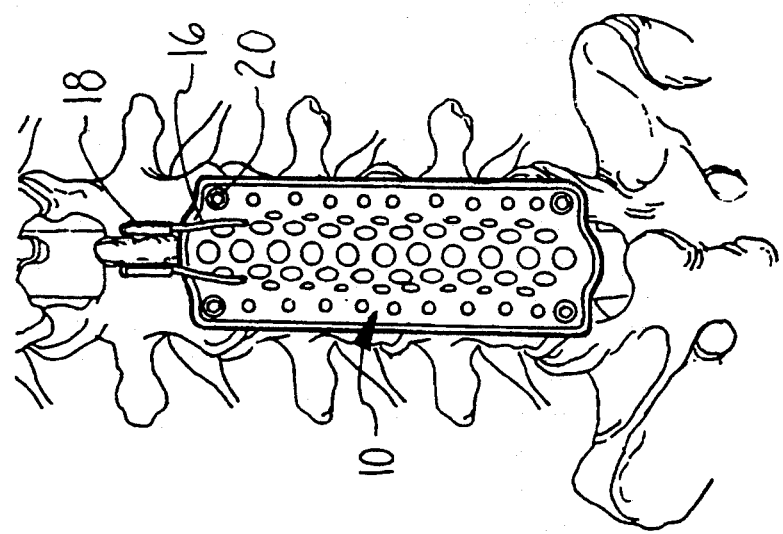
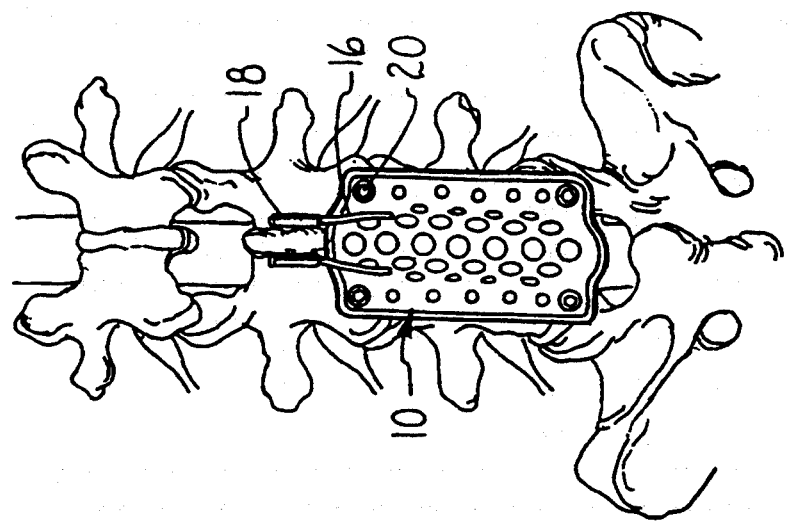
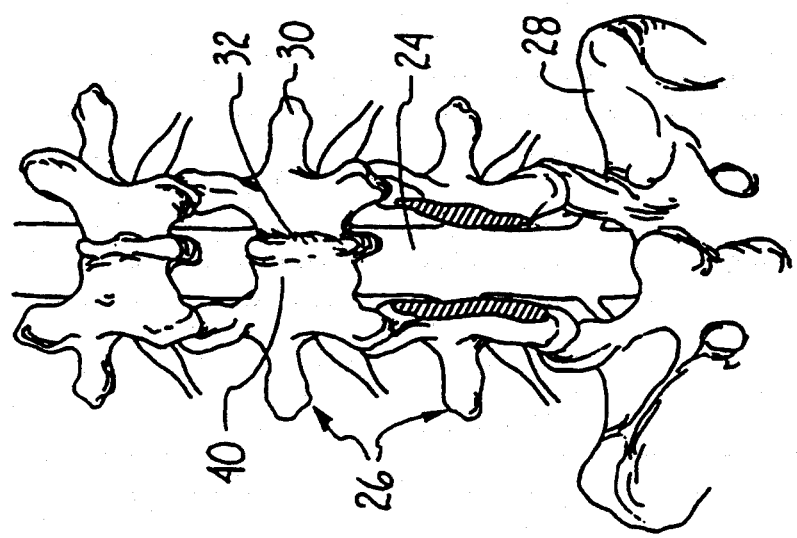

SPINAL CORD PROTECTION DEVICE

This application is a continuation of application Ser No. 07/975,106, filed Nov. 12, 1992, now abandoned.

FIELD OF THE INVENTION

This invention relates generally to orthopedic surgical devices, and more specifically to a surgical device suitable for covering a bony dissection in a patient and to methods for protecting a patient's spinal dura and methods for preventing the development of scar tissue following a bony dissection in a vertebrate.

BACKGROUND OF THE INVENTION

Many times, an unfortunate consequence of modern back surgery, whether lumbar, thoracic, or cervical surgery, is the formation of post-operative scar tissue. Scar formation surrounding the dura and nerve roots oftentimes will compress the nerve roots and cauda equina, thereby producing neural complications such as persistent low back pain, sciatica, and/or bowel and bladder dysfunction. Multiple revision operations may prove necessary due to recurrent disk herniation, post-operative spinal stenosis (iatrogenic or acquired), or because of exuberant epidural fibrosis.

Scar tissue formation after laminectomies and laminotomies for disk excision or a decompressive laminectomy for spinal stenosis present both surgeon and patient with an additional post-operative concern. Laminectomies and laminotomies frequently remove bone tissue and leave the dura exposed. Post laminectomy scar tissue, also termed epidural fibrosis, is primarily formed from fibrous connective tissue and develops in the post-operative hematoma that forms between the paraspinous muscles and the dura. The dura is relatively thin and can easily be injured during surgery. In particular, the dura is susceptible to damage during revision surgery when scar tissue adheres to the dura making it difficult for the surgeon to perform an adequate neurolysis. Thus, a method is needed for protecting the dura from scar tissue adhesion.

At the present time methods to minimize the amount of scar tissue include the use of autogenous fat grafts, gelatin foams or sponges, or microfibullary collagen as an interposing protective layer between the spinal dura and the adjacent viscera. Other biological substances and chemical compounds that have been tested experimentally for their usefulness in animals include bone grafts, microfibrillar collagen, elastase, polyethylene, mylar, dacron, teflon and methylmethacrylate.

Autogenous fat grafts have been used following laminectomies as early as 1964. The fat is placed over the exposed dura after removal of the lamina or a portion of the lamina. The fat provides a protective barrier for the dura, and may limit scar formation between the muscle and the dural tissue. However, fat grafts are known to frequently adhere to the dura. These adhesions complicate revision surgery because they require tedious dissection by the orthopaedic or neurosurgeon. Fat grafts are preferably harvested from a sight close to the surgical incision, such as the subdermal areolar tissue bed. However, unless the patients are overweight, fat harvesting from nearby locations is not always possible, particularly in multiple laminectomy procedures. Further, fat harvesting may require a second incision. The incisions at the secondary locations may sometimes lead to complications such as hematoma formation or dimpling in the skin.

Other substances are used where fat grafts are not possible or desired. Gelatin foam (such as Gelfoam ® sponge, supplied by Upjohn Company Inc., Kalamazoo, Mich.), or polylactic acid (PLA) is a useful substitute for autogenous fat grafts. This material is also placed over the dura to reduce scar formation. There is some controversy concerning the preference of gelatin foams or sponges versus fat; however, neither is optimal. Like fat, gelatin foams or sponges may move out of position following surgery. Furthermore, while fat and gelatin foams may form a barrier between the visceral tissue and the dura, there is a propensity for both fat and gelatin foam or sponge to adhere to the dura. Neither fat nor gelatin foam provides adequate physical protection to the cauda equina.

A mechanical barrier that would provide support to the spinal dura as well as reduce scar formation is needed. U.S. Pat. No. 4,013,078 to Feild discloses a device for preventing adhesions between the patient's dura and spinal nerves and other anatomic structures following spinal surgery. The device includes a conduit sheath of teflon or silicone that is positioned in close proximity to the nerve root. Like the previous protective overlay substances, such a device is invasive to the neuroforamen and anchors directly to the dura. This in turn would promote adhesions between the dura and the protecting device creating unnecessary complications for revision surgery.

In order to minimize the surgical time for dissection, minimize nerve injury and minimize dural tears a spinal cord protection device should be simple to insert, non-invasive to the dura and maintain a distance from the neural tissues. Preferably, anchoring means should contact bone instead of tissue prone to scar formation to minimize post-operative epidural fibrosis. Finally, the optimal mechanical device is readily contoured to provide a customized mechanical barrier to prevent dural or nerve root injury. Preferably, the device is adaptable in design to accommodate other surgical devices used in back surgery. Such a device is provided in the detailed description of this invention.

SUMMARY OF THE INVENTION

The biocompatible protection device in accordance with the present invention comprises a shield that is adapted to cover a bony dissection in a vertebrate. The shield is prepared from a biocompatible material, and is preferably attached to bone.

In a preferred embodiment of the present invention, the invention relates to a spinal cord protection device prepared from a biocompatible material. The device is designed to cover the bony dissection of a vertebrae following hemilaminectomy, laminectomy surgery or the like.

In one embodiment of this invention a biocompatible protection device is provided to prevent the postoperative formation of adhesions. The shield is adapted to cover a bony dissection in a vertebrate and the shield includes means for attaching the shield to bone. Preferably the device is fenestrated and is molded to conform to the bone surrounding the bony dissection. The device is preferably prepared from a biocompatible material. The biocompatible material is preferably prepared from a thermoplastic polymer. In a preferred embodiment, the shield includes a radiopaque material and is preferably impregnated with a scar-retarding substance. In yet another preferred embodiment, the shield is prepared in a color that contrasts with the colors of the viscera and skeletal tissue.

In another preferred embodiment of this invention, the invention relates to a biocompatible protection device to prevent the postoperative formation of adhesions comprising a shield adapted to cover at least a portion of one vertebrae, wherein the shield is positioned along the posterior surface of the vertebral column. Preferably the shield contains fenestration and attachment means suitable to affix the shield to the vertebral column. The shield is preferably molded to conform to the contours of the vertebrae and the device is prepared in a number of different dimensions to accommodate bony dissections of at least one, two or three vertebrae. In a particularly preferred embodiment, the device is adapted to fit over the bony dissection associated with either a hemilaminectomy or a laminectomy.

In another embodiment of this invention, a device is provided for protecting the spinal dura following the bony dissection of a vertebrae comprising a shield adapted to cover the posterior surface of at least a portion of one vertebrae and attachment means associated with the shield for affixing the shield to the vertebrae. The attachment means for affixing the shield to the vertebrae is at least one attachment arm. In another embodiment the attachment means for affixing the shield to the vertebrae are attachment pins and in addition, the attachment means includes sutures attaching the fenestrations to the vertebrae.

In addition, this invention relates to a method for preventing adhesions to the spinal dura following spinal surgery comprising performing a bony dissection on at least a portion of one vertebrae and positioning the device of the spinal cord protection device to cover the bony dissection. In a preferred embodiment, the method additionally comprises the step of affixing the device to at least one vertebrae. Various other objects, advantages, and features of the present invention will become readily apparent from the ensuing detailed description, and the novel features will be particularly pointed out in the appended claims.

BRIEF DESCRIPTION OF THE DRAWINGS

FIG. 3A is a partial perspective view of lumbar vertebrae illustrating the bony dissection associated with a laminectomy;

FIG. 3B is a partial perspective view, similar to FIG. 3A, showing use of the shield device to cover the laminectomy defect in accordance with the present invention;

FIG. 3C is a partial perspective view showing the use of an elongated shield device to cover a laminectomy defect associated with two vertebrae;

DETAILED DESCRIPTION OF THE PREFERRED EMBODIMENT

Back surgery including laminectomies, hemilaminectomies spinal stenosis surgery, and diskectomies, including microdiskectomies, involve the removal of vertebral bone tissue to gain access to the spinal foramen. This bone removal leaves the spinal dura exposed and unprotected. Following surgery, scar tissue frequently forms between the dura and the surrounding tissue. Research indicates that the epidural scar is principally formed from fibroblasts derived from the damaged erector spinae muscles that overlay the laminectomy site (LaRocca, et al. *J. Bone Joint Surg.* 56B:545–550, 1974). These cells form adhesions that bind the muscle tissue to the fragile dura. As a result of adhesion formation, spinal mobility is reduced and the adhesions often lead to pain and slow post-operative recovery. The device of this invention advantageously operates to prevent adhesion formation and to physically protect the dura, now exposed by surgery. In addition, the device of this invention facilitates future revision surgery.

While this invention will be discussed as it relates to spinal surgery, it is contemplated within the scope of this invention that the shield of this invention is suitable as a protective covering for any bony dissection in a vertebrate. Therefore, while a preferred embodiment of this invention relates to the use of the shield to cover a bony dissection of a vertebrae, the shield device could similarly be used to cover a bony dissection associated with open heart surgery, the bony dissection of the cranium, or the like. Those with skill in the art of orthopaedics or neurosurgery will be able to generate formed shields, anchorable to bone, that will accommodate bony dissections in a variety of skeletal tissues.

Figure 1:
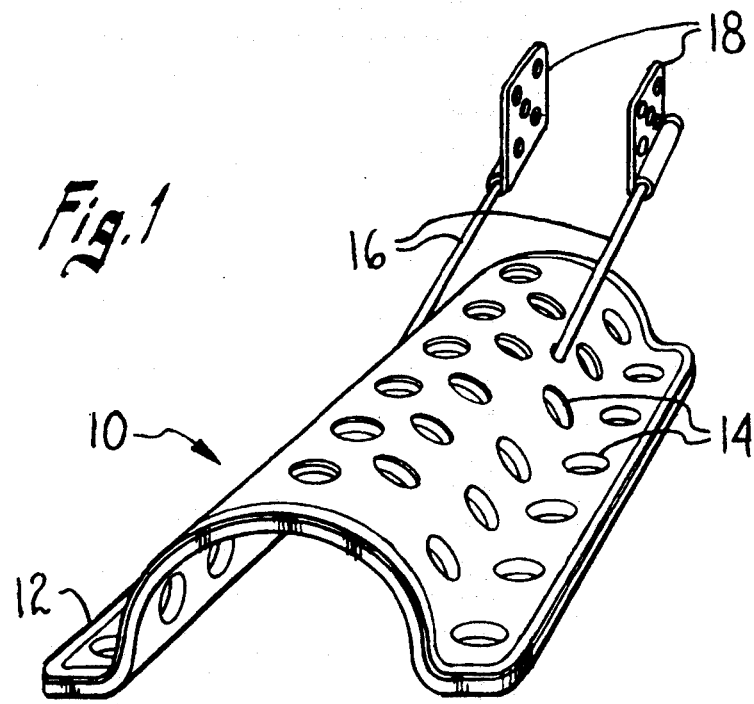
FIG. 1 is a right-front perspective view of the preferred embodiment, showing the arched shield and attachment arms.

FIG. 1 provides an exemplary drawing of a preferred embodiment of this invention. The invention provides a formed shield 10 adapted to fit onto at least one vertebral facet (not shown in FIG. 3) to cover the bony dissection associated with a hemilaminectomy procedure, a laminectomy procedure or the like. As diagrammed in FIG. 1, a main body 11 of the shield 10 is molded or formed preferably as an arch or semi-cylinder. The arch flattens out on each side of the main body 11, forming a pair of support planes 12. The support planes 12 provide a surface area suitable for resting the shield 10 against the vertebral bone. The arched contours of the main body 11 prevent contact of the main body 11 with the spinal dura or nerve roots, thereby minimizing further trauma to the spinal dura and preventing the formation of adhesions and scar tissue between the underside of the device and the spinal dura.

Figure 4B:
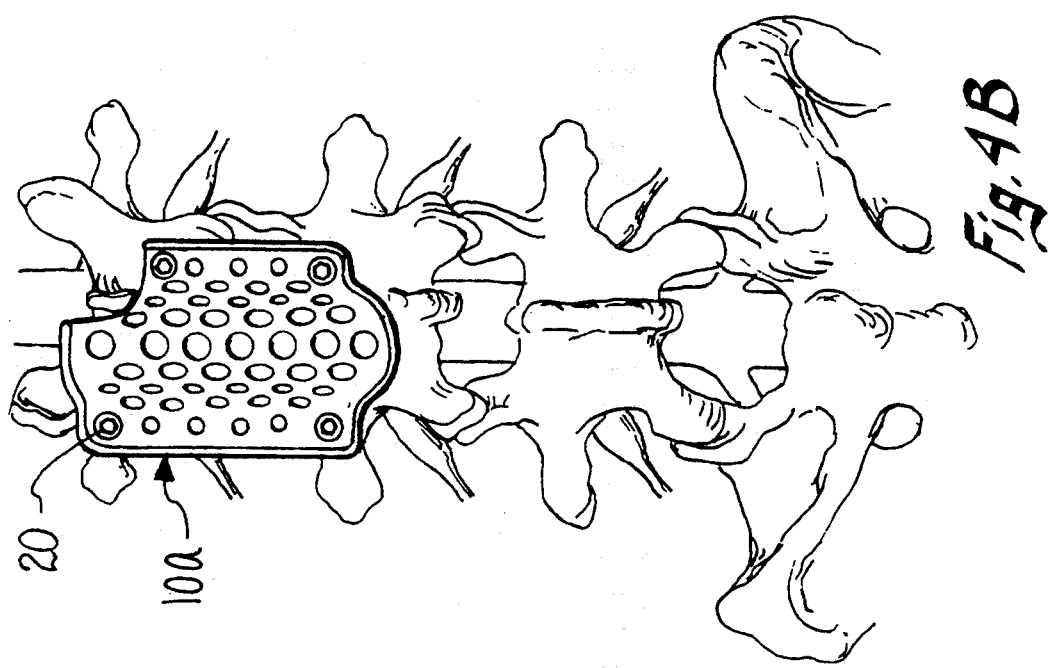
FIG. 4B is a partial perspective view, similar to FIG. 4A, showing use of the shield device to cover the hemilaminectomy defect in accordance with the present invention.

As will be discussed in the context of FIGS. 4 and 5, the removal of vertebral bone along the spinal column leaves the cauda equina susceptible to physical trauma. Products such as gelatin foam or fat do not provide a sufficient barrier to prevent potential physical trauma. The shield 10 of the present invention advantageously rests on bone to minimize the contact between the device and the spinal dura and surrounding neural tissues.

Such reduced contact minimizes adhesion formation between the neural tissues and the device itself.

In a preferred embodiment of this invention, a plurality of fenestrations 14 are formed in the surface of the shield 10. It is contemplated within the scope of this invention that the fenestrations 14 may take any number of forms or shapes, and those depicted in the figures are to be viewed as exemplary. The fenestrations 14 are distributed across the surface of the shield 10 and are designed to prevent the retention of fluid within the vertebral canal. Absent such openings, liquids such as cerebral spinal fluid, blood, and irrigation fluid associated with surgery could potentially accumulate beneath the shield 10 and create harmful pressure on the cauda equina and associated neural tissue. Following surgery the fenestrations 14 serve as out-flow ports to relieve pressure associated with the accumulation of fluid beneath the device during the healing process. Optionally, the fenestrations 14 may be covered with a filter, mesh, or the like (not shown), to prevent the extension of scar tissue formation into the fenestrations 14 while permitting the passage of fluid through the shield 10.

In another preferred embodiment of this invention, the device is associated with a surgical drain (not shown) to further facilitate fluid egress from the surgical site. Such surgical drains are well known in the art and it is contemplated that the device of this invention is adapted to accommodate a drain or in another embodiment a drain is directly incorporated into the device.

When positioned correctly over the bony dissection, it is unlikely that the shield 10 would move. Thus although not necessary to the function of the present invention, it is understood that most surgeons would likely prefer to anchor the shield 10 in place following surgery.

The attachment means contemplated for use with the shield 10 of the present invention can take any number of forms. In a preferred embodiment, the attachment is to bone. Bone attachment contemplated within the scope of this invention include, but are not limited to, both attachment to adjacent spinous processes and lateral attachments such as to facets, transverse processes, articulating processes or the like. It is desirable that no contact is made with the neural elements. Preferably, the attachment means does not extend into the spinal canal or neuroforamen to an extent that would make contact with the dura or nerve roots likely.

Figure 2:
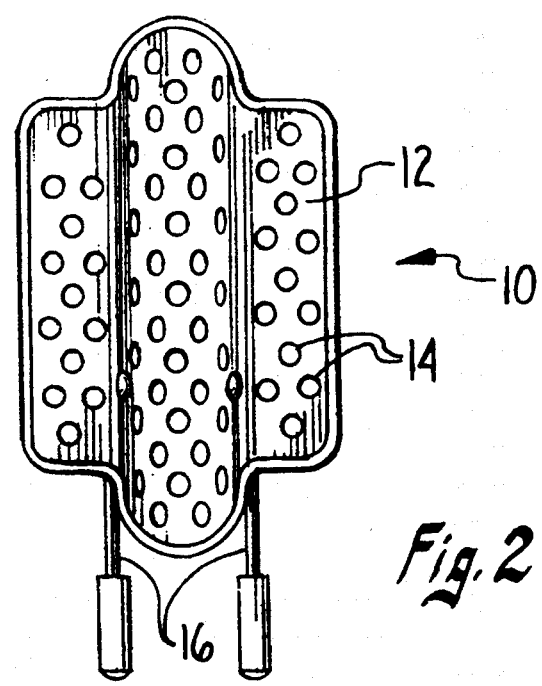
FIG. 2 is a bottom plan view showing the arched shield and attachment arms of FIG. 1.

In a preferred embodiment, the attachment means is a pair of attachment arms 16 attached to the main body 11 of the shield 10. Preferably, each of the attachment arms 16 comprise a rod 17 that is attached to and extends, at an acute angle, from the main body 11 of the shield 10. In this embodiment, the rods 17 are used to attach the shield 10 to an inferior or superior spinous process (see FIGS. 4A and 4B). The actual attachment to the spinous process may take any form known in the art. In a preferred embodiment the rods 17 terminate in a pair of attachment flags 18. As shown in FIG. 1, the flags 18 are provided with a plurality of pin holes 19 to facilitate their attachment to an adjacent spinous process. In another embodiment, the attachment means is through the use of surgical wire, staples or the like. The pins, wire or other attachment means contemplated within this invention, whether in the form of the rods 17 or otherwise, are prepared from surgical steel, tungsten, titanium or other suitable materials. FIG. 2 clearly illustrates the manner in which the attachment means laterally extend beyond the "footprint" of the main body 11.

Advantageously, the fenestrations 14 may also serve as attachment means. For example, suture or wire is useful for attaching the shield 10 to bone by being passed through the fenestrations 14, binding the shield 10 to adjacent bone. Similarly, it is contemplated that in such cases where necessary, the shield 10 is stabilized to cartilage ligament or adjacent muscle tissue. In either case, the fenestrations 14 ably serve as anchoring points over the entire surface of the shield 10, as required.

The actual dimensions of the shield 10 will vary depending on the particular surgical procedure. In a preferred embodiment, the device is prepared in a size and shape to accommodate a laminectomy. Laminectomies are used for spinal stenosis surgery, for central disk herniation, for an osteophyte centrally, for intradural tumors or for other conditions such as epidural abscesses. Laminectomies result in the exposure of the right and left nerve root axilla and the central cauda. The application of the device to a bony dissection following a laminectomy procedure is illustrated in FIG. 3A, 3B and 3C.

FIG. 3A is an illustration of a laminectomy of the fifth lumbar vertebrae. A spinal cord 24 is schematically depicted, surrounded by a veretebial column composed of individual lumbar vertebrae 26, and the sacrum 28. Although the shape of the individual vertebrae 28 does vary, each are composed of a transverse process 30 and a spinous process 32.

A preferred application of the shield 10 is provided in FIG. 3B. The shield 10 is positioned over the laminectomy site and the attachment arms 16, terminating here, in attachment flags 18, are used to attach the device to the spinous process 32 of the fourth lumbar vertebrae 26. In addition to the attachment arms 16, in this embodiment a set of four attachment pins 20 are used to anchor the four corners of the shield 10 in place to the surrounding vertebrae tissue.

FIG. 3C illustrates another preferred embodiment of the invention. In FIG. 3C, the shield 10 is designed to span a laminectomy defect involving two vertebrae. Attatchment arms 16 and attachment flags 18 are similarly positioned on the shield 10 of FIG. 3C. In this embodiment, the shield 10 is adapted to span at least two vertebrae. It is contemplated that the shield 10 is prepared in a length and width to accomodate laminectomies involving three or more vertebrae.

In the embodiment illustrated in FIGS. 3A and 3B, it is contemplated that the overall length of the shield 10 will be at least as long as a lateral length l of the lamina surface of the vertebrae 26 containing the laminotomy defect, and wide enough to stably mate with the remaining lateral lamina surfaces of bone following the laminectomy procedure. Therefore, it is contemplated that the overall length of the shield 10 for use in spanning one laminectomy defect (or hemilaminectomy defect, see FIGS. 4A and 4B) ranges in size from about 2.0 cm to 6.0 cm and preferably between 2.5 cm to 4.5 cm, with a final width ranging from about 1.5 cm to 4.5 cm, and preferably between about 2.0 cm to 3.5 cm.

Customization of the final size and shape of the shield 10 by the surgeon will produce a size suitable for each individual patient. The optimal thickness of the shield 10 will vary depending on the plasticity or moldability of the device, which in turn will depend on the choice of shield material. However, it is contemplated that a preferred thickness of the shield 10 should be approximately 0.5 mm to 8 mm and more preferably, about 0.5 mm to 5 mm.

Figure 4A:
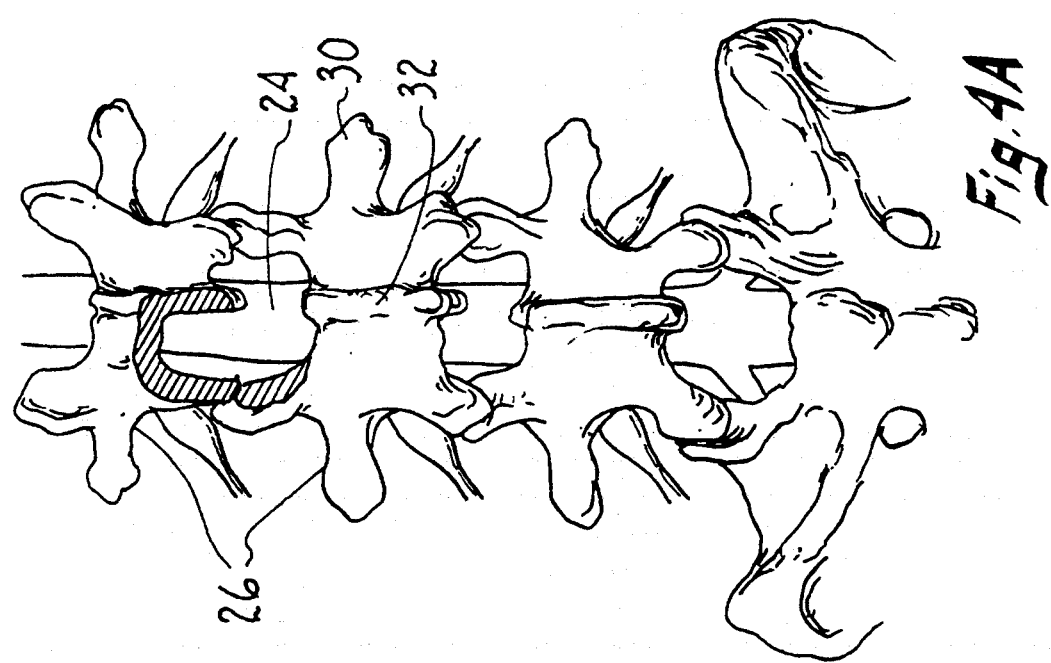
FIG. 4A is a partial perspective view of lumbar vertebrae illustrating the bony dissection associated with a hemilaminectomy.
Figure 5:
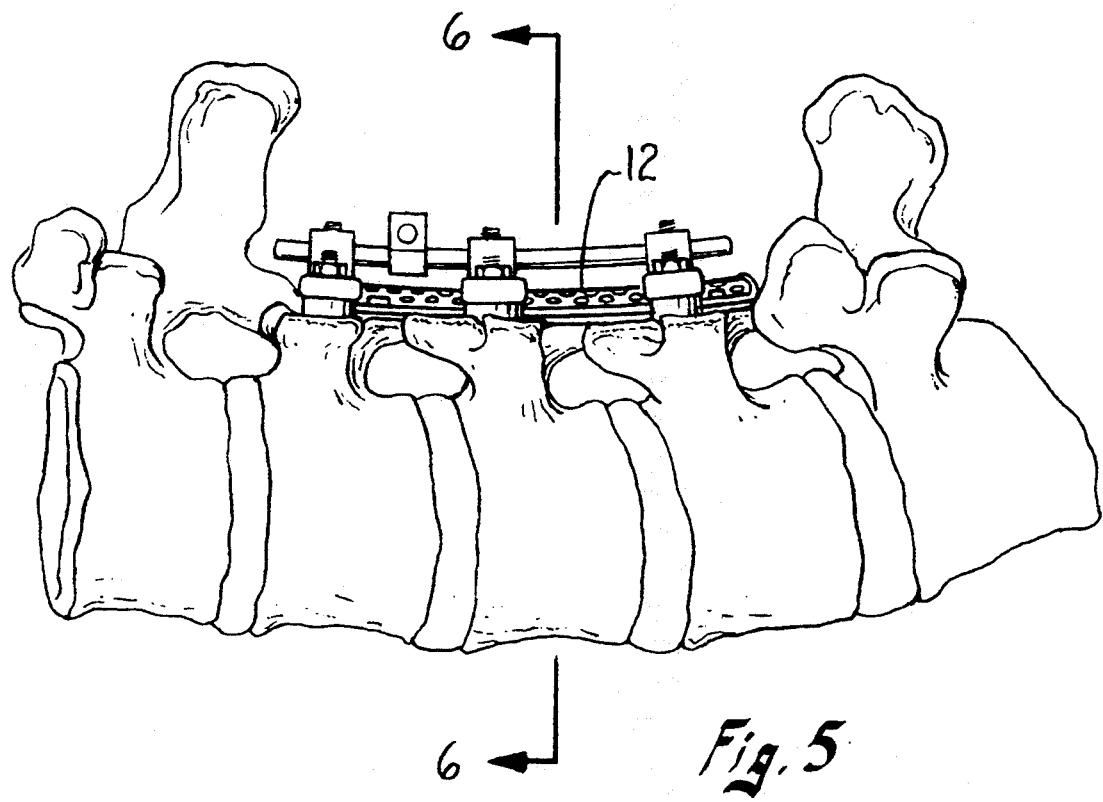
FIG. 5 is a partial side perspective view lumbar vertebrae showing another preferred embodiment of the present invention.

FIG. 4A provides an illustration of the bony dissection associated with a hemilaminectomy. Since the dissection for a hemilaminectomy is smaller than that of a laminectomy, it is contemplated that the surgeon using a scalpel, or the like will be able to readily customize the shield 10 as sized for the laminectomy to overlie the exposed dura after a hemilaminectomy procedure. An example of a customized shield 10a contemplated for use in a hemilaminectomy is provided in FIG. 4B. The customized shield 10a is attached to the vertebrae 26 using the set of attachment pins 20. Alternatively, it is contemplated that the shield 10 of FIG. 1 could be customized for a hemilaminectomy by removing one of the attachment arms 16. The remaining attachment arm 16 serves as an attachment means to anchor the shield 10 to a superior or an inferior spinous process.

It is further contemplated that the overall length of the shield 10 can be varied to accommodate laminectomies or hemilaminectomies involving more than one vertebrae. Thus, for example, in a laminectomy procedure involving the third, fourth and fifth lumbar vertebrae, the shield is preferably about 6.0 cm to about 12 cm in length and more preferably about 6.5 cm to about 9 cm in length. The width is preferably about 2.0 cm to 5.0 cm and more preferably about 2.0 cm to 3.5 cm.

As illustrated in FIG. 1, the main body 11 of the shield 10 preferably has an arch shape, and height h that prevents contact between the spinal dura and the surface of the shield 10. Preferably, the height h of the arch is between about 0.2 cm and 4.5 cm from the support planes 12, although within this range, it is contemplated that the shield 10 will be manufactured in at least two separate ranges of arch heights.

Figure 6:
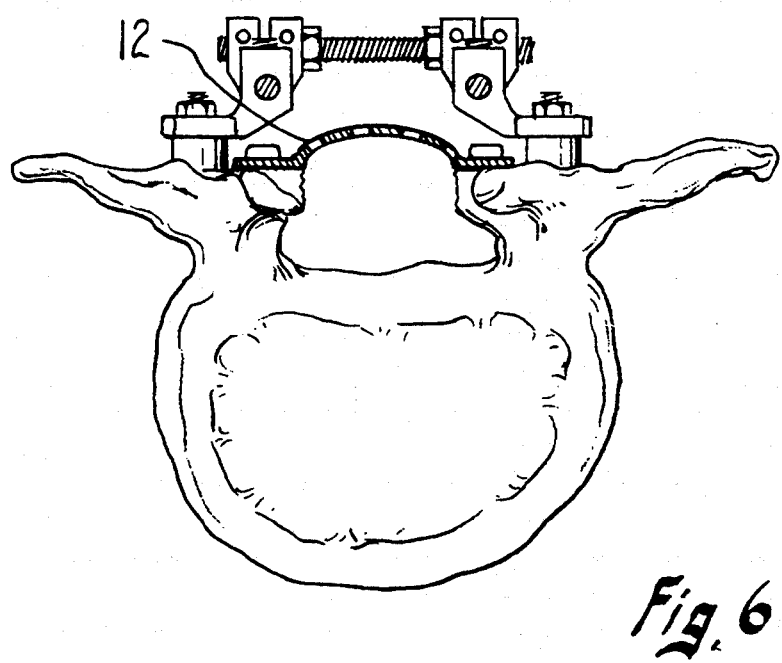
FIG. 6 is a sectional view taken substantially along the line 6—6 of FIG. 5, showing the positioning of the arched shield in accordance with a preferred embodiment of the present invention.

It is further contemplated that the arch height h can be varied to accommodate other medical devices known in the art. In a particularly preferred embodiment, the height h of the arch is between about 0.2 cm to 1.5 cm, or about one-half the height of an adjacent spinous process when positioned on the patient, and is used with medical devices such as a Dynamic Transverse Traction ("DTT") unit or other instrumentation systems employing a plurality of pedicle screws 34, (see FIG. 5) such as the Steffee-VSP system (AcroMed Corporation), Isola instrumentation (AcroMed Corporation, Cleveland, Ohio), or the like. The use of the shield 10 with such a device is illustrated in FIG. 5 in side view and in FIG. 6 in cross-section.

DTTs are particularly useful where lumbar segmental instability is a problem. The pedicle screws 34 and transverse rods 36 associated with these devices tend to restrict the placement of a spinal cord protective device over the spinal canal. The shield 10 that is suitable for a DTT device, or the like, preferably has a height h smaller than the dimension of the height between the DTT construct and the exposed dura. The reduced arch size permits the positioning of the spinal cord protection device beneath the pedical screws 34 and the transverse rods 36 without impingement. In such a case, the shield 10 is anchored to the vertebrae 26 through the fenestrations 14. Alternatively, the shield 10 may be anchored at its periphery to the adjacent facets or spinous processes 32 above or below the decompression, using anchoring pins together with the anchoring means associated with the fenestrations 14.

It is contemplated that the shield 10 of this invention may be prepared from any number of materials known in the art. It is contemplated that the device could be prepared from surgical steel including a woven metal fiber or other similar material. In a preferred embodiment of this invention, the device is prepared from a thermoplastic polymer such as polypropylene, polyethylene, polymethacrylate or the like. Other materials contemplated for use in this invention include, but are not limited to, tungsten, titanium, polytetrafluoroethylene, silicone, bioerodable polylactic acid, hydroxylapatite, regenerated collagen or the like. Those with skill in the art of medical devices will be readily able to select and formulate a composition having the preferred characteristics herein described.

Preferably, the material is biocompatible and is capable of being cut with a standard surgical tool, such as a scalpel, knife or scissors to permit customization of the device in the operating room to the shape and size of the bone defect for each individual patient. Methods for manufacturing the device of this invention will depend on the choice of material. Those with skill in the art of manufacturing implantable medical devices will be readily able to use the description of the invention provided herein to produce the contemplated spinal cord protection device. Thus, the device of this invention can be tooled, molded, heat pressed or the like. It is further contemplated that, depending on the selection of material for manufacturing the device of this invention, the device may have some pliability, such that the surgeon can customize the device to fit the desired bony dissection and, in addition, the shield 10 can be further bent or molded by the surgeon to accommodate the particular topography of the patient's spine.

The device of this invention may be prepared from a solid sheet of material, or the device can advantageously be prepared as a laminate. For those embodiments where the device is a composite of laminated sheets, it is possible to include or incorporate a radiopaque material as a laminated sheet into the device. Similarly the shield material can be impregnated with a radiopaque substance or incorporate a radiopaque material into the edges of the device. Suitable radiopaque materials include metals or halogenated compounds such as iodinated or brominated compounds. Other compounds include barium containing substances, renografin or commercially available, Isovue ® (Squibb Diagnostics, Princeton, N.J.). Thus, the polymers contemplated for use in preparing the shield of this invention are preferably halogenated or are prepared in combination with halogenated polymers.

The presence of a radiopaque material in the shield 10 permits visualization of the shield 10 by X-ray radiation or the like. In situations where the patient's back pain persists or where revision surgery is contemplated, the surgeon is able to determine the position of the shield device of this invention prior to or during the revision surgery. The radiopaque substance also allows the surgeon to verify the location of the bone dissection as determined from the position of the shield.

It is further contemplated that the shield 10 of the invention can advantageously be impregnated with, or otherwise positioned in place in association with, a drug suitable for inhibiting the formation of adhesions. Therefore, in another preferred embodiment, the shield contains an absorptive, saturatable or impregnatable material suitable for acting as a carrier for an adhesion-inhibiting substance. Suitable adhesion-inhibiting drugs contemplated for use in association with the shield 10 of this invention include, but are not limited to, heparin salts and analogs of heparin salts, such as Pentosan Polysulfate ("PPS", available, for example, from Sigma Chemical Company, St. Louis, Mo.) or the like, or growth factor inhibitors or other compounds recognized in the art to inhibit adhesion formation. Further, compounds such as gelatin foams such as Gelfoam® sponge or Avitene® (MedChem, Inc. Woodburn, Mass.) can additionally be used together with the shield 10 of this invention to further reduce the incidence of adhesions following surgery.

One of the important advantages of this invention, over gelatin foams and other materials used in the art, is that the device facilitates revision surgery. Revision surgery is complicated by the formation of adhesions to the spinal dura. Dissections of adhesions and scar formation increase the time the patient must be under anaesthesia. Moreover, dissection of the scar tissue can result in inadvertent pierces or tears in the dura and the release of spinal fluid into the surgical area that can further complicate surgery. The spinal cord protection device prevents adhesions with the dura. During revision surgery, the surgeon can cut through the muscle and facia to the device quickly without the potential of piercing or tearing the spinal dura.

To further facilitate revision surgery, it is contemplated that in another preferred embodiment of this invention, the shield 10 is colored. It is contemplated that the selected dye will contrast in color with bone, blood or internal tissues, and thus further facilitate revision surgery since the surgeon can rapidly identify the shield 10 during the dissection process. Thus, contrasting colors contemplated for use with this device include shades of blue, green, black, purple, yellow, orange or the like.

While this invention is described in association with lumbar vertebrae, it is contemplated that the shield 10 of this invention is suitable for the cervical and thoracic regions of the spine as well. Further, as disclosed supra, the shield 10 is contemplated for use in any location in the body associated with a bony dissection.

The shield 10 of the present invention is contemplated to be commercially available in a number of different sizes, shapes and include various attachment means. The shields preferably are packaged in separate sterile packaging and can be arranged on a tray that includes single and multiple protector devices in different sizes and embodiments.

An exemplary surgical procedure employing the shield 10 of this invention is provided in Example 1, below. This procedure is only exemplary. Surgeons skilled in the art of orthopaedics and neurosurgery will be readily able to adapt their surgical techniques and surgical procedures to include the use of this shield and in particular, those surgeons skilled in spinal surgery will readily appreciate the variations discussed herein that do not detract from the scope of this invention.

Particular embodiments of the invention will be discussed in detail and reference has been made to possible variations within the scope of the invention. There are a variety of alternative adaptations and surgical procedures available to those of skill in the art which would similarly permit one to successfully produce and use the intended invention.

EXAMPLE 1

Laminectomy and Decompression Surgery Involving the Surgical Positioning of the Spinal Cord Protection Device The surgical tools disclosed herein are standard surgical equipment well known to those skilled in the art of orthopaedic and neurosurgery. The patient is positioned on an Andrew's frame or operating table and prepped and draped in the fashion standard for back surgery. The incision is made over the spinous process of the area to be decompressed. The incision is carried down through the dorsal lumbar fascia and the fascia is then incised down to the spinal lamina junction. Dissection is continued out to the tips of the transverse processes and is accomplished using the electrocautery and Cobb dissection tool. Self retaining retractors are then placed into the wound to allow clear visualization of the structures which have been denuded of their soft tissue. Further meticulous soft tissue dissection is performed with the removal of the supraspinous ligament and the interspinous ligament for the vertebral levels to be addressed in the surgery process. Intraoperative lateral x-ray confirms the position at the appropriate level. A Lexzell rongeur is then used to remove the bone of the spinous process 32 and that portion of the lamina 40 (see FIG. 3A). A Kerrison rongeur is used to remove bone from the lamina as well as ligamentum flavum and epidural fat.

The dissection is carried out to the facet joints. If nerve root entrapment, either by disk or soft tissue is noted lateral to the facet, then a partial medial facetectomy is performed. The origin of the nerve roots are then identified and traced into their corresponding neural foramen.

A neural foraminal probe is placed into the neural foramen at each level and if it is met with any impedance, a partial foraminotomy is performed at each level to facilitate the passage of the probe. Once this is completed, hemostasis is achieved using the Malis bipolar coagulator or electrocautery device.

Dissection into the neural foramen many times can result in increased instability by weakening the facet region. In order to minimize this, a 4 mm burr is used to do the dissection in the opening of the neural foramen to minimize the destruction with the Kerrison rongeur. The operative area is then irrigated and suction dried, and once again hemostasis is achieved using electrocautery and a Malis bipolar coagulator.

Following the corrective surgery to the spinal column, the spinal cord protection shield 10 is positioned over the laminectomy defect (see FIG. 3B). Customization of the shield 10 is performed with a scalpel and scissors thereby molding the shield 10 to conform with the individual contours of the spinal column. The angle of the attachment arms relative to the protector device is adjusted by manually deforming the attachment arms to facilitate their attachment to an adjacent spinous process. The arms are sutured in place onto the spinous process and the fenestrations on the shield body are additionally used to suture the device in place (see FIG. 3B).

The wound is closed using standard operating procedures, a drain is preferably placed into the wound and, as one example of wound closure, the wound is closed in layers using a #1 Vicryl (Ethicon, Piscataway, N.J.)

suture for the dorsal lumbar fascia, a 2-0 Vicryl for the deep subcutaneous tissue, and a 3-0 subcuticular stitch.

While particular embodiments of the invention have been described in detail, it will be apparent to those skilled in the art that these embodiments are exemplary rather than limiting, and the true scope of the invention is that defined in the following claims.

What is claimed is:

1. A method for minimizing adhesions to the spinal dura following spinal surgery, comprising the steps of:
    performing a bony dissection on at least a portion of one vertebrae to expose the spinal dura: and
    positioning a biocompatible protection device to cover said exposed spinal dura, wherein said device comprises a shield adapted to cover at least a portion of one vertebrae having said bony dissection, an elongate concavity on a first side of the shield, said concavity extending axially from a first axial end of the shield to a second axial end of the shield; a first support plane on the shield; spaced laterally apart in a first direction from the longitudinal axis of the shield; and a second support plane on the shield, spaced laterally apart in a second direction from the longitudinal axis of the shield; wherein placement of said first and second support planes on opposite sides of said spinal dura aligns the longitudinal axis of said concavity generally parallel to the longitudinal axis of the spinal dura, with said first side of the shield spaced apart from the spinal dura, and wherein placement of said device over said dura minimizes adhesions to said dura.

2. The method of claim 1, additionally comprising the step of affixing said device to at least one vertebrae.

3. The method of claim 1, wherein the device is positioned over more than one vertebrae.

4. The method of claim 1, wherein the positioning step additionally includes the step of adding an adhesion minimizing agent between the device and the dura.

5. The method of claim 4, wherein the adhesion minimizing agent is incorporated into the device.

6. The method of claim 1, wherein the method additionally comprises the step of exposing the device in a subsequent surgical procedure.

7. The method of claim 6, wherein the method further comprises the step of removing said device to reexpose said spinal dura.

* * * * *